United States Patent [19]

Razzano

[11] Patent Number: 5,935,590

[45] Date of Patent: Aug. 10, 1999

[54] FINGERNAIL LACQUER COMPOSITION AND METHOD OF APPLICATION

[76] Inventor: Dominick D. Razzano, 5902 NW. 40th Ter., Virginia Gardens, Fla. 33166

[21] Appl. No.: 09/021,652

[22] Filed: Feb. 10, 1998

[51] Int. Cl.⁶ .............................. A61K 6/00; A61K 7/00; A61K 7/04

[52] U.S. Cl. .............................................. 424/401; 424/61

[58] Field of Search ........................................ 424/61, 401

[56] References Cited

U.S. PATENT DOCUMENTS 4,166,054  8/1979  Meeske et al. ...................... 260/23 EP

*Primary Examiner*—Thurman K. Page
*Assistant Examiner*—Sharon Howard
*Attorney, Agent, or Firm*—Robert M. Downey, P.A.

[57] ABSTRACT

The composition includes a pigment and a binder; the pigment being present in a pigment volume concentration of between 69% to 75% of the non-volatile portion of the composition to create a physical action upon drying of a layer of the composition applied to fingernails and toe nails, wherein a lack of cohesive strength between the pigment and binder results in shrinking of the applied layer to form cracks, thereby visibly exposing a previously applied underlying nail polish through the formed cracks.

9 Claims, 1 Drawing Sheet

FINGERNAIL LACQUER COMPOSITION AND METHOD OF APPLICATION

BACKGROUND OF THE INVENTION

1. Field of the Invention

The present invention relates to a cosmetic preparation and method for applying the preparation to fingernails and toe nails.

2. Description of the Related Art

The art is crowded with various nail polish compositions and methods of applying nail art designs to fingernails. Such methods and compositions are no longer limited to a single, uniform color of nail polish applied to all of one's fingernails or toe nails. It is now commonplace to paint multi-color designs on each nail, sometimes adding sparkles, decals, and other design elements to enhance the overall appearance of the polished nails. This is usually done by airbrushing or free hand painting, both of which require a considerable degree of skill and artistic ability. For this reason, anything beyond conventional polishing of nails with a uniform color must usually be done by a professional at a nail salon.

Now that nail art has gone beyond the traditional single color and french manicure, new and more unusual appearances are becoming increasingly popular. The crackle appearance which results using the composition of the present invention is similar to an appearance known in the furniture industry for creating an antique finish. However, the crackle lacquer used in the furniture industry is not suitable for use in the cosmetic industry, as it contains a number of toxic components which present a health hazard. For this reason, crackle lacquers presently known in the art are not approved by the Food and Drug Administration for use as a cosmetic product. And, while others may have attempted to achieve the crackle effect in a nail polish composition, it is believed that such attempts have been unsuccessful due to the difficulty in producing a non-toxic crackle composition which has physical characteristics that make it suitable for application by both brushing and spraying on fingernails and toe nails.

Accordingly, there is a need in the cosmetic industry for a non-toxic lacquer composition for application to fingernails and toe nails, either by brushing or spraying, and wherein the lacquer composition is physically structured to provide a crackle appearance upon drying. In fulfilling this need, the present invention provides for a non-toxic cosmetic preparation and method of applying the preparation to fingernails and toe nails, wherein the cosmetic preparation is structured to undergo a physical change upon drying to produce a crackle appearance.

SUMMARY OF THE INVENTION

The present invention is directed to a cosmetic preparation and a method of applying the cosmetic preparation to fingernails and toe nails. The cosmetic preparation includes a crackle composition for application to nails which have one or more coats of previously applied conventional colored nail polish thereon. This crackle composition includes a pigment and a binder provided in a ratio to create a physical action upon drying of a layer applied to the nails, wherein a lack of cohesive strength between the pigment and the binder results in shrinking of the applied layer to form cracks therein. The previously applied underlying colored nail polish is thus visible through the cracks formed in the overlying layer of the crackle composition which is of a different color.

Depending upon the surface quality and chemical composition of the conventional fingernail polish which has been applied before application of the cosmetic preparation of the present invention, it may be necessary to apply a clear coat barrier composition in covering relation to the fingernail polish prior to application of the crackle coat composition. This colorless, transparent base composition can be either brushed or sprayed on the fingernails to provide a layer covering the surface of the fingernail polish. After allowing the base coat to dry for three to five minutes at ambient temperature, the crackle coat composition is applied. The crackle coat composition can be either brushed or sprayed on the nails to provide a uniform layer thereon. Upon air drying for five to ten minutes, cracking of the applied crackle coat occurs and two colors become visible; the color of the crackle coat and the color of the conventional fingernail polish which appears through the cracks of the crackle coat layer.

To obtain a high gloss over the crackle coat, a conventional clear gloss layer can be brushed or sprayed over the crackle coat layer after the crackle coat layer has completely dried. For the highest gloss, two coats of clear gloss lacquer can be applied.

BRIEF DESCRIPTION OF THE DRAWINGS

For a fuller understanding of the nature of the present invention, reference should be made to the following detailed description taken in connection with the accompanying drawings in which.

DETAILED DESCRIPTION OF THE PREFERRED EMBODIMENT

Figure 1:
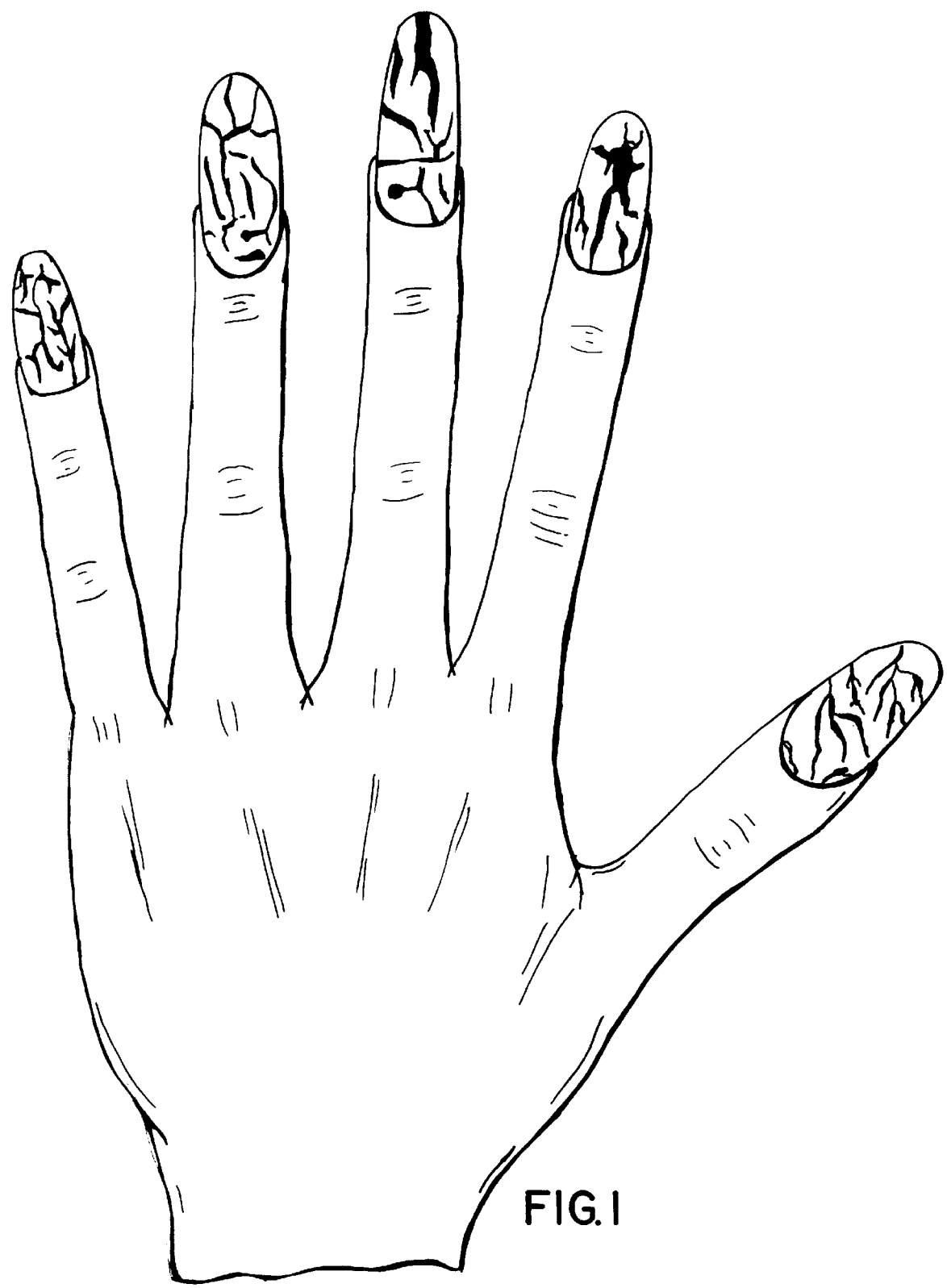
FIG. 1 is a top plan view of a hand having fingernails treated with the cosmetic preparation of the present invention, wherein each of the nails is shown with a different crackle coat pigment and nail polish color combination to illustrate various appearances achieved using the cosmetic preparation of the present invention.

The cosmetic preparation of the present invention provides a novel and distinct visual appearance on polished fingernails. In contrast to the one solid color appearance produced by conventional fingernail polish products, the cosmetic preparation of the present invention produces two colors with a randomly created crackle design. More specifically, the top crackle coat appears as one color while a different color of the underlying coat of conventional nail polish is visible through the cracks formed in the top crackle coat, as seen on the fingernails in FIG. 1.

The cosmetic preparation of the present invention is useful in combination with virtually any commercially available fingernail polish. The cosmetic preparation includes two separate compositions which are applied independently of the other by either brushing or spraying. Specifically, the cosmetic preparation includes a clear coat base composition which is applied to the surface of dry colored fingernail polish which has been previously painted on the fingernails or toe nails. The clear coat base composition is applied in a uniform layer by either brushing or spraying over the surface of the polished nails, and allowed to dry for five to ten minutes at ambient temperature.

The cosmetic preparation further includes a crackle coat composition which comprises non-toxic ingredients, including color pigments which are FDA certified for cosmetic purposes. In particular, the liquid or vehicle portion of the crackle coat composition is free from toluol, methyl ethyl ketone, xylol, and formaldehyde. The crackle coat composition is applied to the exposed, dry surface of the base coat by either brushing or spraying. The applied layer of the crackle coat should be uniform across the entire upper side of the nails. Upon drying for a period of five to ten minutes at ambient temperature, the applied layer of crackle coat begins to form random cracks, thereby exposing the color of the underlying conventional nail polish. This phenomenon of cracking of the crackle coat layer is a physical reaction which results from over pigmentation. More specifically, the crackle coat composition includes a pigment and a binder which are provided in a ratio that creates a lack of cohesive strength between the pigment and binder. This results in shrinking of the applied layer of the crackle coat composition when drying, thereby creating the desired cracks. Ideally, the pigment is present at a pigment volume concentration (pvc) of between 69% to 75%, wherein the pvc is the percentage of pigment in the non-volatile portion of the formula.

In many instances, the clear coat base composition can be omitted, depending upon the surface quality and chemical composition of the particular fingernail polish which has been previously applied to the nails. However, to ensure a uniform foundation for subsequent coatings, application of the clear coat base composition is generally recommended prior to applying the crackle coat composition.

The following examples are illustrative of compositions of the cosmetic preparation of the present invention.

EXAMPLE 1

A clear coat base composition, comprising petroleum naphtha, n-butyl acetate, ¼ sec nitrocellulose, a plasticizer, propylene glycol methyl ether acetate, and ethyl acetate was prepared with the following ingredients in the indicated concentrations:

| Ingredient | Weight | Gallons | Supplier |
| --- | --- | --- | --- |
| Petroleum naphtha (VMP) | 105.720 lbs. | 17.388 | Shell Chemical Co. Houston, TX |
| n-butyl acetate | 135.770 lbs. | 18.598 | Eastman Chemical Kingsport, TN |
| ¼ sec nitro-cellulose (70%) | 93.000 lbs. | 8.942 | Hercules Wilmington, DE |
| Isopropyl alcohol | 21.500 lbs. | 3.307 | Eastman Chemical Kingsport, TN |
| 2-ethylhexyl diphenyl phosphate (Santicizer 141) | 9.500 lbs. | 1.044 | Monsanto Springfield, MA |
| #15 Castor Oil | 3.000 lbs. | 0.350 | Cas Chemical Bayonne, NJ |
| Propylene glycol methyl ether acetate (P.M.A.) | 25.800 lbs. | 3.108 | Dow Chemical Midland, MI |
| Ethyl acetate | 18.770 lbs. | 2.536 | Eastman Chemical Kingsport, TN |
| TOTAL | 413.060 lbs. | 55.273 (1 drum) | |

Description: A one drum batch (413 pounds) of the clear coat base composition was prepared in accordance with the following procedure. The ingredients, as listed above, are added, one at a time, in the order presented, beginning with petroleum naphtha. After adding each ingredient, the mixture is stirred until the added ingredient is completely blended with the previously added ingredients. This process of adding and stirring in each ingredient is continued until all ingredients have been completely blended in a homogenous mixture. The resultant mixture is then thinned using butyl acetate and a brushing viscosity of 35 secs. No. 2 Zahn Cup is achieved.

EXAMPLE 2

A crackle coat composition, in accordance with a preferred embodiment of the present invention, comprises a first mixture portion and a second mixture portion. The pigment in the crackle composition consists of amorphous silica, magnesium silicate (both in the first mixture portion) and a color component (in the second mixture portion) and is present in a preferred pigment volume concentration (pvc) to produce shrinking and cracking of an applied layer of the composition upon drying. The crackle coat composition was prepared with the following ingredients in the indicated concentrations:

| Ingredient | Weight | Gallons | Supplier |
| --- | --- | --- | --- |
| First Mixture Portion | | | |
| n-butyl acetate | 42.30 lbs. | 5.74 | Eastman Chemical Kingsport, TN |
| Petroleum naphtha (VMP) | 21.50 lbs. | 3.55 | Shell Chemical Co. Houston, TX |
| 70 sec nitro-cellulose (70%) | 5.50 lbs. | 0.53 | Hercules Wilmington, DE |
| Isopropyl alcohol | 11.40 lbs. | 1.83 | Eastman Chemical Kingsport, TN |
| Maleated-Rosin (Beckacite 111) | 3.80 lbs. | 0.42 | Arizona Chemical Panama City, FL |
| Propylene glycol methyl ether acetate (P.M.A.) | 7.60 lbs. | 0.92 | Dow Chemical Midland, MI |
| Dipropylene glycol methyl ether (D.P.M.) | 5.60 lbs. | 0.71 | Dow Chemical Midland, MI |
| Mineral spirits | 7.10 lbs. | 1.09 | Shell Chemical Houston, TX |
| Amorphous silica (OK 412) | 4.50 lbs. | 0.25 | Degussa Corp. Ridgewood, NJ |
| Magnesium silicate (Vantalc 6H) | 46.20 lbs. | 2.05 | R.T. Vanderbilt Norwalk, CT |
| Ethyl acetate | 17.90 lbs. | 2.42 | Eastman Chemical Kingsport, TN |
| Second Mixture Portion | | | |
| FD&C Blue Al Lake Code 10-21-DB2803 (Color component) | 2.73 lbs. | 0.34 | Hilton Davis Newark, NJ |
| Maleated-Rosin (Beckacite 111) | 2.00 lbs. | 0.22 | Arizona Chemical Panama City, FL |
| m-butyl acetate | 11.30 lbs. | 1.55 | Eastman Chemical Kingsport, TN |
| Acrylic resin (Acryloid B72) | 1.06 lbs. | 0.11 | ROHM & Haas Midland, MI |
| Dipropylene glycol methyl ether (D.P.M.) | 10.00 | 1.12 | Dow Chemical Midland, MI |
| Ethyl acetate | 5.00 | 0.67 | Eastman Chemical Kingsport, TN |
| TOTAL | 205.43 lbs. | 23.52 | |

Description: A 23½ gallon batch of the crackle coat composition can be prepared in accordance with the following procedure. The ingredients of each mixture portion, as listed above, are added, one at a time, in the order presented, beginning with n-butyl acetate. After adding each ingredient, the mixture portion is stirred until the added ingredient is completely blended with the previously added ingredients. This process of adding and stirring in each ingredient is continued until all ingredients have been completely blended to form a homogenous mixture. The first and second mixture portions are then combined and stirred until completed blended, creating a final homogenous composition.

The final composition is thinned using butyl acetate to achieve the desired viscosity. The preferred viscosity for brushing application is 35 secs. No. 2 Zahn Cup. For a spraying viscosity, the composition should be thinned to a viscosity of 20–25 secs. No. 2 Zahn Cup.

While the above example provides for a blue color component, it is recognized that any FDA certified color component can be used in the pigment mixture.

While the instant invention has been described in accordance with preferred embodiments thereof, it is recognized that departures from the instant disclosure may be made within the spirit and scope of the present invention, and which departures shall not be limited except as set forth in the following claims and under the doctrine of equivalents.

What is claimed is:

1. A cosmetic lacquer composition for application to fingernails and toe nails comprising:
   a binder consisting of non-toxic, skin compatible ingredients;
   a pigment consisting of non-toxic, skin compatible ingredients; and
   the volume of concentration of said pigment in said composition causing the formation of random cracks in a layer of said composition when applied to a surface and upon drying of said applied layer.

2. A lacquer composition for application to fingernails and toe nails comprising:
   a first mixture comprising n-butyl acetate, petroleum naphtha, 70 sec nitrocellulose (70%), isopropyl alcohol, maleated-rosin, propylene glycol methyl ether acetate, dipropylene glycol methyl ether, mineral spirits, amorphous silica, magnesium silicate, and ethyl acetate; and
   a second mixture comprising color component, maleated-rosin, n-butyl acetate, acrylic resin, dipropylene glycol methyl ether, and ethyl acetate.

3. A lacquer composition as recited in claim 2 wherein a pigment in said composition comprises the color component, amorphous silica, and magnesium silicate.

4. A lacquer composition as recited in claim 3 wherein the pigment is present in a pigment volume concentration of between 69% to 75% of a non-volatile portion of said composition.

5. A cosmetic preparation for application to fingernails and toe nails comprising:
   a base composition comprising petroleum naphtha, n-butyl acetate, ¼ sec nitrocellulose (70%), isopropyl alcohol, 2-ethylhexyl diphenyl phosphate, #15 castor oil, propylene glycol methyl ether acetate, and ethyl acetate; and
   a crackle lacquer composition comprising:
      a first mixture comprising n-butyl acetate, petroleum naphtha, 70 sec nitrocellulose (70%), isopropyl alcohol, maleated-rosin, propylene glycol methyl ether acetate, dipropylene glycol methyl ether, mineral spirits, amorphous silica, magnesium silicate, and ethyl acetate; and
      a second mixture comprising a color component, maleated-rosin, n-butyl acetate, acrylic resin, dipropylene glycol methyl ether, and ethyl acetate.

6. A cosmetic preparation as recited in claim 5 wherein a pigment in said composition comprises the color component, amorphous silica, and magnesium silicate.

7. A cosmetic preparation as recited in claim 6 wherein the pigment is present in a pigment volume concentration of between 69% to 75% of a non-volatile portion of said composition.

8. A method of manufacturing a cosmetic lacquer composition comprising the steps of:
   providing a binder portion consisting of non-toxic, skin compatible ingredients;
   providing a pigment portion consisting of non-toxic, skin compatible ingredients; and
   combining said binder portion and said pigment portion so that said pigment portion is present in a volume of concentration which causes the formation of random cracks in an applied layer of said cosmetic lacquer composition upon drying thereof.

9. A method of decorating fingernails and toe nails comprising the steps of;
   providing a cosmetic lacquer composition comprising:
      a binder portion consisting of non-toxic, skin compatible ingredients;
      a pigment portion consisting of non-toxic, skin compatible ingredients;
   applying a layer of said cosmetic lacquer composition to a surface on a nail;
   drying said applied layer; and
   allowing random cracks to form in said applied layer.

* * * * *